(12) United States Patent
Hwang et al.

(10) Patent No.: US 9,546,963 B2
(45) Date of Patent: Jan. 17, 2017

(54) INSPECTION DEVICE FOR PAINTED SURFACE OF VEHICLE

(71) Applicants: Hyundai Motor Company, Seoul (KR); Kia Motors Corporation, Seoul (KR); Digital Imaging Technology, Inc., Hwaseong-si, Gyeonggi-do (KR)

(72) Inventors: Sang Ki Hwang, Hwaseong-si (KR); Jinho Seok, Daegu (KR)

(73) Assignees: Hyundai Motor Company, Seoul (KR); Kia Motors Corporation, Seoul (KR); Digital Imaging Technology, Inc., Hwaseong-si (KR)

( * ) Notice: Subject to any disclaimer, the term of this patent is extended or adjusted under 35 U.S.C. 154(b) by 353 days.

(21) Appl. No.: 14/144,368

(22) Filed: Dec. 30, 2013

(65) Prior Publication Data
US 2015/0002653 A1    Jan. 1, 2015

(30) Foreign Application Priority Data

Jun. 27, 2013   (KR) ......................... 10-2013-0074851

(51) Int. Cl.
*G01N 21/88*    (2006.01)

(52) U.S. Cl.
CPC ...... *G01N 21/8851* (2013.01); *G01N 21/8803* (2013.01)

(58) Field of Classification Search
CPC ................................................ G01N 21/8851
See application file for complete search history.

(56) References Cited

U.S. PATENT DOCUMENTS

| | | | | |
|---|---|---|---|---|
| 3,985,444 A | * | 10/1976 | Takashima | G01B 11/165 356/32 |
| 5,237,404 A | * | 8/1993 | Tanaka | G01B 11/303 348/128 |
| 5,369,488 A | * | 11/1994 | Morokuma | G01B 11/002 356/493 |
| 6,573,987 B2 | * | 6/2003 | Shires | G01N 21/88 348/126 |
| 7,394,531 B2 | * | 7/2008 | Tirosh | G01N 21/8903 250/208.1 |
| 7,869,061 B2 | * | 1/2011 | Sato | G01B 11/2536 356/603 |

(Continued)

FOREIGN PATENT DOCUMENTS

| | | |
|---|---|---|
| JP | 7-306150 A | 11/1995 |
| JP | 2005-24284 A | 1/2005 |
| KR | 10-2011-0080725 A | 7/2011 |

*Primary Examiner* — William C Vaughn, Jr.
*Assistant Examiner* — Luis Perez Fuentes
(74) *Attorney, Agent, or Firm* — Morgan, Lewis & Bockius LLP

(57) ABSTRACT

An inspection device for painted surface with a base layer and a clear layer painted on the base layer of a vehicle includes a frame mounted to an arm of a robot, a line scan camera, a first light source lighting up at a predetermined angle is provided thereto, which is mounted to the frame, and the line scan camera which acquires first vision data through the regular reflection light from the painted surface using the light of the first light source, and a controller which receives the first vision data from the line scan camera and detects surface defect of the painted surface according to the first vision data.

9 Claims, 5 Drawing Sheets

(56) References Cited

U.S. PATENT DOCUMENTS

| | | | | |
|---|---|---|---|---|
| 9,031,734 B2* | 5/2015 | Froom | ............... | B64F 5/0045 |
| | | | | 701/29.3 |
| 2004/0095573 A1* | 5/2004 | Tsai | ............... | G01N 21/8806 |
| | | | | 356/237.5 |
| 2006/0184040 A1* | 8/2006 | Keller | ............... | A61B 5/0059 |
| | | | | 600/476 |
| 2015/0002653 A1* | 1/2015 | Hwang | ............ | G01N 21/8803 |
| | | | | 348/86 |

* cited by examiner

INSPECTION DEVICE FOR PAINTED SURFACE OF VEHICLE

CROSS-REFERENCE TO RELATED APPLICATION

The present application claims priority to Korean Patent Application No. 10-2013-0074851 filed on Jun. 27, 2013, the entire contents of which is incorporated herein for all purposes by this reference.

BACKGROUND OF THE INVENTION

Field of the Invention

The present invention relates to an inspection device a vehicle. More particularly, the present invention relates to an inspection device for painted surface of a vehicle.

Description of Related Art

In the manufacturing process of an automobile, since painting process determines anticorrosive and appearance quality of a vehicle, the painting process of a vehicle is relatively complicated including an electroplating, primer coating, base coating, clear coating and so on.

Electroplating is a process that uses electrical current to reduce dissolved metal cations so that they form a coherent metal coating on an electrode.

The main functions of the primer are to act as leveler, as a protector and make it easier to apply the base coat for the component it's applied on.

The base coat is applied after the primer coat. This coat contains the visual properties of color and effects, and is usually the one referred to as the paint. The base coat is in the automotive industry mainly divided into two categories, solid and metallic.

Usually sprayed on top of a colored basecoat, clearcoat is a glossy and transparent coating that forms the final interface with the environment. For this reason, clearcoat must be durable enough to resist abrasion and chemically stable enough to withstand UV light. Clearcoat can be either solvent or water-borne.

After painting processes, visual inspection for a vehicle body is conducted. In the visual inspection, dust, scratch and so on is checked.

When poor quality of painting is detected, amending works such as re-painting, polishing are conducted.

In the visual inspection, human's vision and tactile sense are used, subjective judgment or fatigability of worker may influence result of the visual inspection.

The information disclosed in this Background of the Invention section is only for enhancement of understanding of the general background of the invention and should not be taken as an acknowledgement or any form of suggestion that this information forms the prior art already known to a person skilled in the art.

BRIEF SUMMARY

Various aspects of the present invention are directed to providing an inspection device for painted surface of a vehicle having advantages of inspecting surface defect and interlaminated defect between painted layers.

In an aspect o the present invention, an inspection device for painted surface with a base layer and a clear layer painted on the base layer of a vehicle may include a frame mounted to an arm of a robot, a line scan camera, wherein a first light source lighting up at a predetermined angle is provided to the line scan camera, and wherein the line scan camera is mounted to the frame, and acquires first vision data through a regular reflection light from the painted surface using a light of the first light source, and a controller which receives the first vision data from the line scan camera and detects surface defect of the painted surface according to the first vision data.

The inspection device may further include a second light source which lights up perpendicular to the painted surface for the line scan camera to acquire second vision data through diffused reflection light from the painted surface, wherein the controller receives the second vision data from the line scan camera and detects interlaminated defect between the base layer and the clear layer of the painted surface according to the second vision data.

The first and the second light sources are on or off alternately with a predetermined time interval by control of the controller.

The inspection device may further include a mirror reflector which is mounted to a side of the frame, reflects an image of the painted surface to the line scan camera, and reflects lights of the first and the second light sources reflected from the painted surface to the line scan camera, and a reflecting plate which is mounted to an another side of the frame, and reflects the lights of the first and the second light source reflected from the painted surface to the painted surface.

The first light source lights up at 45 degree on vertical direction of the mirror reflector.

The line scan camera takes photographs of images of the painted surface reflected by the mirror reflector.

The mirror reflector and the reflecting plate are rotatably mounted to the frame respectively.

The second light source is rotatably mounted to the frame.

The inspection device may further include a first moving unit which is disposed to the frame for the line scan camera to be moved along lighting up direction of the first light source, and a second moving unit which is disposed to the frame for the second light source to be moved.

The light lighting up by the first light source is reflected to the painted surface by the mirror reflector, the light regular reflected by the painted surface is reflected to the painted surface by the reflecting plate, the light reflected by the painted surface is reflected to the line scan camera by the mirror reflector, the line scan camera take photographs of the image of the painted surface reflected by the mirror reflector, and the controller analyses the first vision data from the line scan camera and detects surface defect of the painted surface according to the first vision data.

The controller detects the surface defect of the painted surface through analyzing difference of light and darkness of the first vision data through the regular reflection light from the painted surface.

The light lighting up by the second light source is lighted to the painted surface and the diffused reflection light from the painted surface is reflected to the painted surface by the reflecting plate, the light reflected by the painted surface is reflected to the line scan camera by the mirror reflector, the line scan camera take photographs of the image of the painted surface reflected by the mirror reflector, and the controller analyses the second vision data from the line scan camera and detects interlaminated defect between the base layer and the clear layer of the painted surface according to the second vision data.

The controller detects the surface defect of the painted surface through analyzing difference of light and darkness of the second vision data.

According to the exemplary embodiment of the present invention, the surface defect and the interlaminated defect between the painted layers of the painted surface may be detected objectively and quickly.

Since the positions of the line scan camera and the second light source may be adjusted for corresponding to various vehicle kinds.

The methods and apparatuses of the present invention have other features and advantages which will be apparent from or are set forth in more detail in the accompanying drawings, which are incorporated herein, and the following Detailed Description, which together serve to explain certain principles of the present invention.

Figure 1:
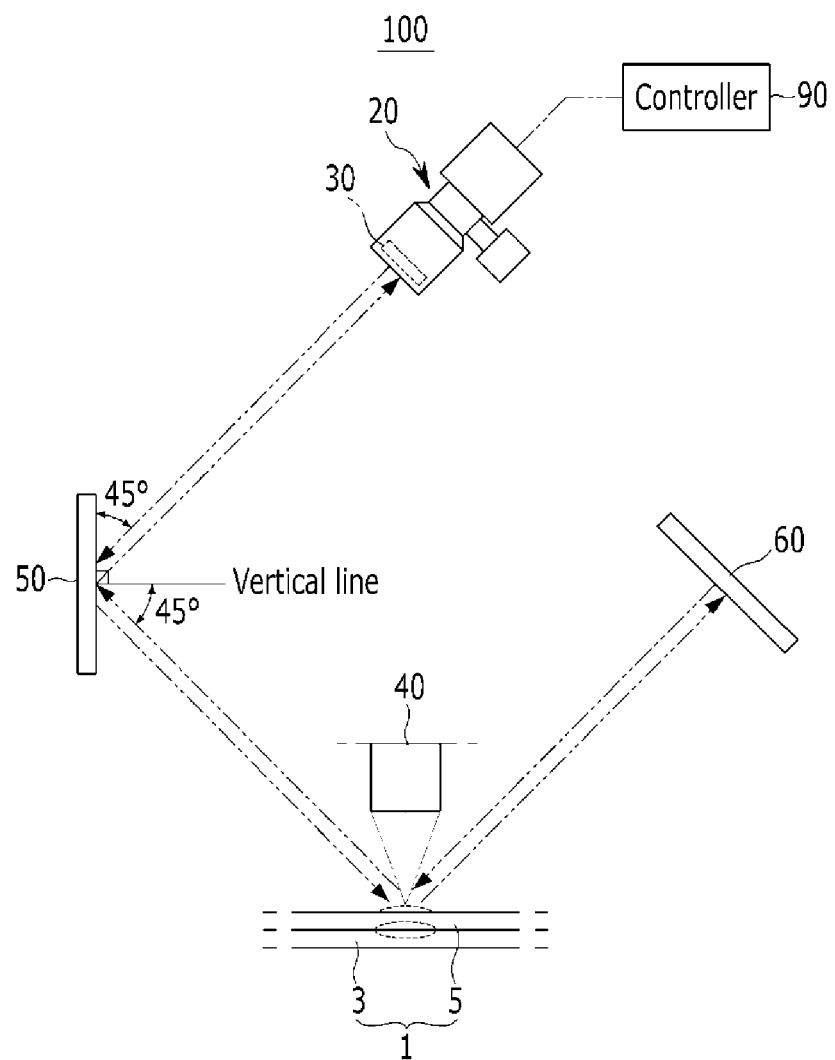
FIG. 1 is a drawing showing an inspection device for a painted vehicle surface according to an exemplary embodiment of the present invention.

It should be understood that the appended drawings are not necessarily to scale, presenting a somewhat simplified representation of various features illustrative of the basic principles of the invention. The specific design features of the present invention as disclosed herein, including, for example, specific dimensions, orientations, locations, and shapes will be determined in part by the particular intended application and use environment.

In the figures, reference numbers refer to the same or equivalent parts of the present invention throughout the several figures of the drawing.

DETAILED DESCRIPTION

Reference will now be made in detail to various embodiments of the present invention(s), examples of which are illustrated in the accompanying drawings and described below. While the invention(s) will be described in conjunction with exemplary embodiments, it will be understood that the present description is not intended to limit the invention(s) to those exemplary embodiments. On the contrary, the invention(s) is/are intended to cover not only the exemplary embodiments, but also various alternatives, modifications, equivalents and other embodiments, which may be included within the spirit and scope of the invention as defined by the appended claims.

The present invention will be described more fully hereinafter with reference to the accompanying drawings, in which exemplary embodiments of the invention are shown. As those skilled in the art would realize, the described embodiments may be modified in various different ways, all without departing from the spirit or scope of the present invention.

In order to clarify the present invention, parts that are not connected with the description will be omitted, and the same elements or equivalents are referred to with the same reference numerals throughout the specification.

Also, the size and thickness of each element are arbitrarily shown in the drawings, but the present invention is not necessarily limited thereto, and in the drawings, the thickness of portions, regions, etc are exaggerated for clarity.

Moreover, the use of the terms first, second, etc. do not denote any order or importance, but rather the terms first, second, etc. are used to distinguish one element from another.

Throughout the specification, unless explicitly described to the contrary, the word "comprise" and variations such as "comprises" or "comprising", will be understood to imply the inclusion of stated elements but not the exclusion of any other elements.

Terms 'unit', 'means', '-er (-or)', 'member', etc, described in the specification indicate a unit for performing at least one function or operation.

FIG. 1 is a drawing showing an inspection device for a painted vehicle surface according to an exemplary embodiment of the present invention.

Referring to FIG. 1, an inspection device for painted surface 100 for a vehicle according to an exemplary embodiment of the present invention may be applied to painting process for an automobile manufacturing system.

The inspection device 100 may be applied to inspection process for detecting defect of appearance of a vehicle after base layer 3 and clear layer 5 are formed to painted surface 1 in base and clear coating processes and dry process in a drying oven.

Hereinafter, appearance defect on the clear layer 5 of the painted surface 1 such as dust, cratering, scratch, pin hole, paint flow, paint splash and so on will be denoted as surface defect, and defect between the clear layer 5 and the base layer 3 of the painted surface 1 such as sanding, spot, concealed defect and so on will be denoted as interlaminated defect between the layers or interlaminated defect between the base layer and the clear layer.

The inspection device 100 according to the exemplary embodiment of the present invention may detect the surface defect on the clear layer 5 and the interlaminated defect between the clear layer 5 and the base layer 3 of the painted surface 1 with different lighting sources.

Figure 2:
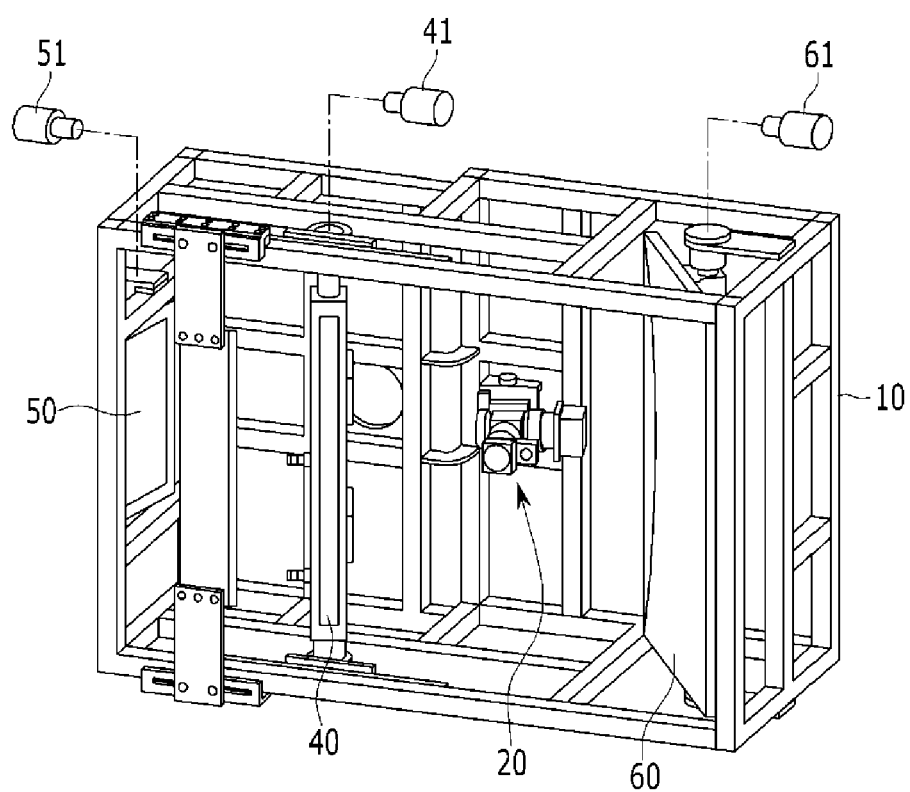
FIG. 2 is a perspective view of an inspection device for a painted vehicle surface according to an exemplary embodiment of the present invention.
Figure 3:
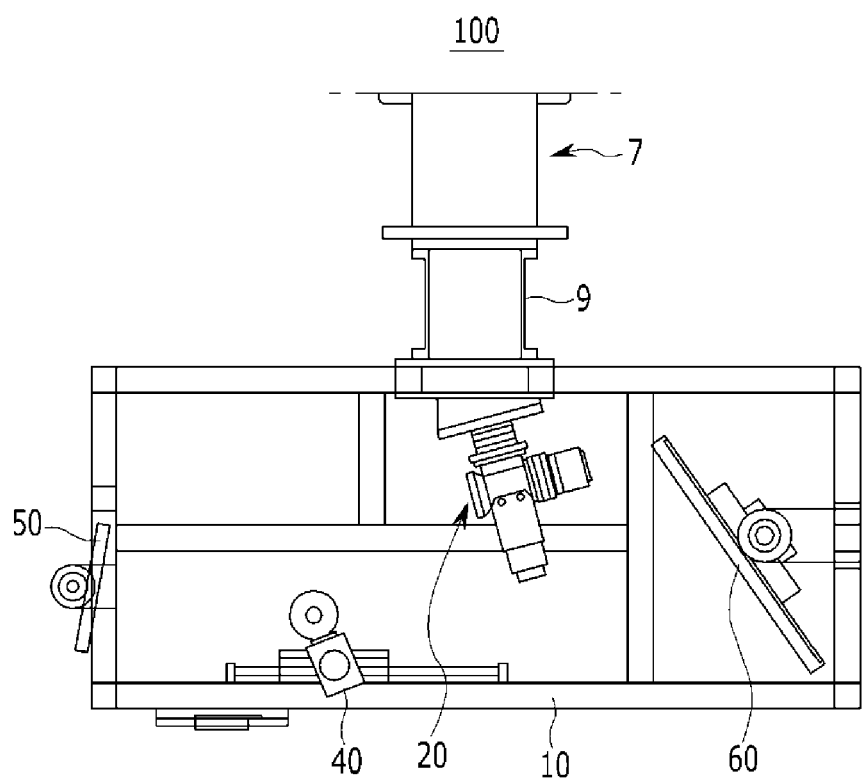
FIG. 3 is a front view showing an inspection device for a painted vehicle surface according to an exemplary embodiment of the present invention.

FIG. 2 is a perspective view of an inspection device for a painted vehicle surface according to an exemplary embodiment of the present invention and FIG. 3 is a front view showing an inspection device for a painted vehicle surface according to an exemplary embodiment of the present invention.

Referring to FIG. 1 to FIG. 3, the inspection device 100 according to the exemplary embodiment of the present invention includes a frame 10, a line scan camera 20 provided with a first light source 30, a second light source 40, a mirror reflector 50, a reflecting plate 60 and a controller 90.

The frame 10 according to the exemplary embodiment of the present invention is selectively mounted to an arm 9 of a robot 7 and may include a tool changer for mounting the frame 10 to the arm 9.

The frame 10 may be equipped with elements such as various types of brackets, support blocks, etc for supporting the above-mentioned components.

Since the above-mentioned elements are for supporting various types of components, they will be referred to collectively as the frame 10, with the exception of some cases, in the exemplary embodiment of the present invention.

The frame 10 may include unit frames each having hexagonal shape.

In the exemplary embodiment of the present invention, the line scan camera 20 may be a vision sensor visually detecting the painted surface and supplying the vision data to the controller 90.

The line scan camera 20 is mounted to the frame 10 and is provided with the first light source 30 lighting up at a predetermined angle to the painted surface 1.

The first light source 30 is mounted around an optical unit of the line scan camera 20. Mounting structure of the line scan camera 20 provided with the first light source 30 will be discussed in detail later.

The line scan camera 20 may acquire first vision data, for detecting the surface defect of the painted surface 1, through the regular reflection light from the painted surface 1 using the light of the first light source 30. And the line scan camera 20 may acquire second vision data, for detecting the interlaminated defect of the painted surface 1, through the diffused reflection light from the painted surface 1 using the light of the second light source 40.

The second light source 40 is mounted to the frame 10 and lights up perpendicular to the painted surface 1 for acquiring the second vision data of the diffused reflection light from the painted surface 1.

The second light source 40 may be rotatable at the frame 10 by the operation of a first motor 41 controlled by the controller 90. The first and the second light source 30 and 40 are on or off alternately with a predetermined time interval by control of the controller 90 for example about 500 μs.

The mirror reflector 50 is mounted one side of the frame 10. The mirror reflector 50 reflects an image of the painted surface 1 to the line scan camera 20, and reflects lights of the first and the second light source 30 and 40 reflected from the painted surface 1 to the line scan camera 20.

The mirror reflector 50 is mounted to the frame 10 and rotatable by the operation of a second motor 51 controlled by the controller 90.

The line scan camera 20 may take photographs of the image of the painted surface 1 reflected by the mirror reflector 50, and the first light source 30 lights up at 45 degree on vertical direction of the mirror reflector 50.

The reflecting plate 60 is mounted to another side of the frame 10. The reflecting plate 60 reflects the lights of the first and the second light source 30 and 40 reflected from the painted surface 1 to the painted surface 1.

The reflecting plate 60 is mounted to the frame 10 and rotatable by the operation of a third motor 61 controlled by the controller 90. The reflecting plate 60 may include a concave distorted surface to reflect reflects the lights of the first and the second light source 30 and 40 reflected from the painted surface 1 to the painted surface 1.

Figure 4:
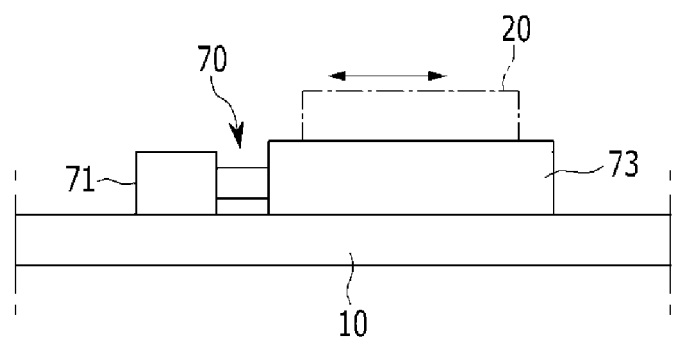
FIG. 4 is a drawing showing a first moving unit of an inspection device for a painted vehicle surface according to an exemplary embodiment of the present invention.

The line scan camera 20 may be movable along lighting up direction of the first light source 30. As shown in FIG. 4, a first moving unit 70 is disposed to the frame 10 for the line scan camera 20 to be moved along lighting up direction of the first light source 30.

The first moving unit 70 include a first drive motor 71 controlled by the controller 90 and a first LM module 73. The line scan camera 20 mounted to the first LM module 73 may be moved along lighting up direction of the first light source 30 by the operation of the first drive motor 71. The first LM module 73 may be a LM guide including a housing, a guide rail, a guide block and a lead screw.

The first moving unit 70 may be constituted by a conventional LM guide obvious to a person skilled in the art, thus detailed description will be omitted.

Figure 5:
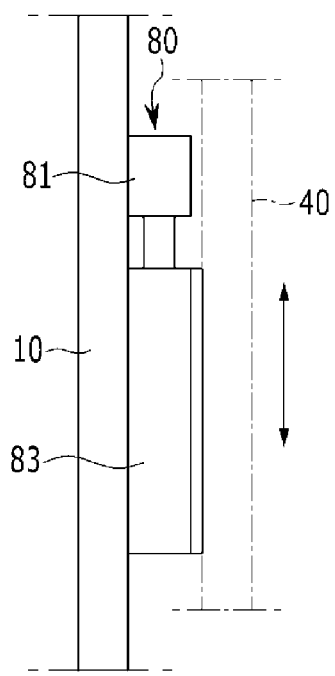
FIG. 5 is a drawing showing a second moving unit of an inspection device for a painted vehicle surface according to an exemplary embodiment of the present invention.

The second light source 40 may be moved at the frame 10. As shown in FIG. 5, a second moving unit 80 is disposed to the frame 10 for the second light source 40 to be moved.

The second moving unit 80 include a second drive motor 81 controlled by the controller 90 and a second LM module 83, and the second light source 40 mounted to the second LM module 83 may be moved by the operation of the second drive motor 81. The second LM module 83 may be a LM guide including a housing, a guide rail, a guide block and a lead screw.

The second moving unit 80 may be constituted by a conventional LM guide obvious to a person skilled in the art, thus detailed description will be omitted.

In the exemplary embodiment of the present invention, the controller 90, as shown in FIG. 1, may control the operations of the line scan camera 20, the first light source 30, the second light source 40, the first, second, and third motor 41, 51, and 61 and the first and the second moving unit 70 and 80.

Also, after the line scan camera 20 acquiring the first vision data through the regular reflection light from the painted surface 1 using the light of the first light source 30, the controller 90 receives the first vision data from the line scan camera 20 and detects the surface defect of the painted surface 1 according to the first vision data.

And after the line scan camera 20 acquiring the second vision data through the diffused reflection light from the painted surface 1 using the light of the second light source 40, the controller 90 receives the second vision data from the line scan camera 20 and detects the interlaminated defect between the layers of the painted surface 1 according to the second vision data.

That is, the controller 90 analyses brightness (difference of the light and darkness) of the first vision data through the regular reflection light from the painted surface 1 and then detects the surface defect of the painted surface 1.

Then controller 90 analyses brightness (difference of the light and darkness) of the second vision data through the diffused reflection light from the painted surface 1 and then detects the interlaminated defect between the layers of the painted surface 1.

Hereinafter, an inspection method using the inspection device according to the exemplary embodiment of the present invention will be discussed.

At a state of mounting the frame 10 to the arm 9 of the robot 7, the frame 10 moves towards the painted surface 1 of a vehicle body by moving the robot 7.

In this case, the line scan camera 20 may move to suitable positions along the lighting up direction of the first light source 30 by the operation of the first moving unit 70 according to various vehicle types. Also, the second light source 40 may move to suitable positions by the operation of the second moving unit 80 according to various vehicle types.

The second light source 40 may be rotated by the operation of the first motor 41 for aligning at suitable position and also the mirror reflector 50 and the reflecting plate 60 may be rotated by the operations of the second and the third motor 51 and 61 corresponding positions to the line scan camera 20 and the second light source 40.

Then, the controller 90 controls the first light source 30 to be on, and controls the second light source 40 to be off for the first light source 30 to light up to the mirror reflector 50. In this case, the first light source 30 lights up at 45 degree on vertical direction of the mirror reflector 50.

The light from the first light source 30 is reflected to the painted surface 1 by the mirror reflector 50, regular reflected at the painted surface 1, and the reflected to the painted surface 1 by the reflecting plate 60.

Then the light is reflected at the painted surface 1 then is reflected to the line scan camera 20 by the mirror reflector 50. The line scan camera 20 takes photographs of the images of the painted surface 1 reflected by the mirror reflector 50 then supplies the first vision data to the controller 90.

The controller 90 receives and analyses the first vision data from the line scan camera 20, and then detects the surface defect on the clear layer 5 of the painted surface 1 such as dust, cratering, scratch, pin hole, paint flow, paint splash and so on.

That is, the controller 90 analyses brightness (difference of the light and darkness) of the first vision data through the regular reflection light from the painted surface 1 and then detects the surface defect of the painted surface 1.

In this case, the controller 90 may subjects the images of painted surface 1 to a binary numbering process, to make a coordinate transformation.

Then the controller 90 analyses brightness (difference of the light and darkness) of the binary numbered first vision data to detect the surface defect of the painted surface 1.

Then, the controller 90 controls the first light source 30 to be off, and controls the second light source 40 to be on with a predetermined time interval for the second light source 40 to light up to the painted surface 1. In this case, the second light source 40 lights up perpendicular to the painted surface 1.

The light lighting up by the second light source is diffused reflected at the painted surface 1, is reflected by the reflecting plate 60 to the painted surface 1, and then is reflected to the line scan camera 20 by the mirror reflector 50. The line scan camera 20 takes photographs of the images of the painted surface 1 reflected by the mirror reflector 50 then supplies the second vision data to the controller 90.

The controller 90 receives and analyses the second vision data from the line scan camera 20, and then detects the interlaminated defect between the base layer 3 and the clear layer 5 of the painted surface 1 such as sanding, spot, concealed defect and so on.

In this case, the controller 90 may subjects the images of painted surface 1 to a binary numbering process, to make a coordinate transformation.

Then the controller 90 analyses brightness (difference of the light and darkness) of the binary numbered second vision data to detect the interlaminated defect of the painted surface 1.

In the exemplary embodiments of the present invention, the line scan camera 20 may take photographs of the painted surface 1 using the first light source 30 for detect the surface defect of the painted surface 1 and also, may take photographs of the painted surface 1 using the second light source 40 for detecting the interlaminated defect between the painted layers 3 and 5 of the painted surface 1.

According to the exemplary embodiment of the present invention, the surface defect and the interlaminated defect between the painted layers of the painted surface may be detected objectively and quickly.

Since the positions of the line scan camera 20 and the second light source 40 may be adjusted for corresponding to various vehicle kinds.

For convenience in explanation and accurate definition in the appended claims, the terms "upper", "lower", "inner" and "outer" are used to describe features of the exemplary embodiments with reference to the positions of such features as displayed in the figures.

The foregoing descriptions of specific exemplary embodiments of the present invention have been presented for purposes of illustration and description. They are not intended to be exhaustive or to limit the invention to the precise forms disclosed, and obviously many modifications and variations are possible in light of the above teachings. They are not intended to be exhaustive or to limit the invention to the precise forms disclosed, and obviously many modifications and variations are possible in light of the above teachings as well as various alternatives and modifications thereof. It is intended that the scope of the invention be defined by the Claims appended hereto and their equivalents.

What is claimed is:

1. An inspection device for painted surface with multiple layers painted on a vehicle comprising:
    a frame mounted to an arm of a robot;
    a line scan camera mounted to the frame;
    a first light source provided to the line scan camera and illuminating at a predetermined angle, line scan camera mounted to the frame and acquiring first image data through a regular reflection light from the painted surface using light from the first light source;
    a second light source inclined from the line scan camera and rotatably mounted to the frame and illuminating perpendicular to the painted surface for the line scan camera to acquire second image data through diffused reflection light from the painted surface;
    a controller receiving the first image data from the line scan camera and detecting a surface defect of the painted surface according to the first image data,
        receiving the second image data from the line scan camera and detecting an interlaminar defect between the base layer and the clear layer of the painted surface according to the second vision data, and
        switching the first and the second light sources on or off alternately with a predetermined time interval;
    a mirror reflector which is mounted to a side of the frame, reflects an image of the painted surface to the line scan camera, and reflects lights of the first and the second light sources reflected from the painted surface to the line scan camera; and
    a reflecting plate which is mounted to an another side of the frame, and reflects the lights of the first and the second light source reflected from the painted surface to the painted surface.

2. The inspection device of claim 1, wherein the first light source illuminates at 45 degree on vertical direction of the mirror reflector.

3. The inspection device of claim 1, wherein the line scan camera takes photographs of images of the painted surface reflected by the mirror reflector.

4. The inspection device of claim 1, wherein the mirror reflector and the reflecting plate are rotatably mounted to the frame respectively.

5. The inspection device of claim 1, wherein the inspection device further comprises:
    a first moving unit which is disposed to the frame for the line scan camera to be moved along illuminating direction of the first light source; and
    a second moving unit which is disposed to the frame for the second light source to be moved.

6. The inspection device of claim 1, wherein:
    the light illuminating by the first light source is reflected to the painted surface by the mirror reflector;
    the light regular reflected by the painted surface is reflected to the painted surface by the reflecting plate;

the light reflected by the painted surface is reflected to the line scan camera by the mirror reflector;

the line scan camera take photographs of the image of the painted surface reflected by the mirror reflector; and the controller analyses the first image data from the line scan camera and detects surface defect of the painted surface according to the first image data.

7. The inspection device of claim 6, wherein the controller detects the surface defect of the painted surface through analyzing difference of light and darkness of the first image data through the regular reflection light from the painted surface.

8. The inspection device of claim 1, wherein:

the light lighting up by the second light source is illuminated to the painted surface and the diffused reflection light from the painted surface is reflected to the painted surface by the reflecting plate;

the light reflected by the painted surface is reflected to the line scan camera by the mirror reflector;

the line scan camera take photographs of the image of the painted surface reflected by the mirror reflector; and the controller analyses the second image data from the line scan camera and detects the interlaminar defect between the base layer and the clear layer of the painted surface according to the second image data.

9. The inspection device of claim 8, wherein the controller detects the surface defect of the painted surface through analyzing difference of light and darkness of the second image data.

\* \* \* \* \*